(12) United States Patent
Yang et al.

(10) Patent No.: US 10,436,746 B2
(45) Date of Patent: Oct. 8, 2019

(54) HIGH PERFORMANCE CHEMICAL AND BIO SENSORS USING METAL OXIDE SEMICONDUCTORS

(71) Applicant: The Regents of the University of California, Oakland, CA (US)

(72) Inventors: Yang Yang, Los Angeles, CA (US); You Seung Rim, Los Angeles, CA (US); Jonathan Yang, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/689,956

(22) Filed: Aug. 29, 2017

(65) Prior Publication Data

US 2018/0059051 A1     Mar. 1, 2018

Related U.S. Application Data

(60) Provisional application No. 62/411,257, filed on Oct. 21, 2016, provisional application No. 62/380,809, filed on Aug. 29, 2016.

(51) Int. Cl.
*G01N 27/407* (2006.01)
*G01N 27/414* (2006.01)
(Continued)

(52) U.S. Cl.
CPC ....... *G01N 27/4146* (2013.01); *A61B 5/1468* (2013.01); *C12Q 1/006* (2013.01);
(Continued)

(58) Field of Classification Search
CPC .. A61B 5/1468; C12Q 1/006; G01N 27/4071; G01N 27/4146; G01N 33/5438; G01N 33/552; B01J 21/00; B01J 23/00
See application file for complete search history.

(56) References Cited

U.S. PATENT DOCUMENTS

| | | | |
|---|---|---|---|
| 8,940,578 B2* | 1/2015 | Facchetti | C23C 18/1216 257/43 |
| 8,940,579 B2* | 1/2015 | Facchetti | C23C 18/1216 257/43 |

(Continued)

OTHER PUBLICATIONS

Allen et al., "Carbon Nanotube Field-Effect-Transistor-Based Biosensorsm," Adv. Mater. 2007, 19, pp. 1439-1451.
(Continued)

*Primary Examiner* — Cam N. Nguyen
(74) *Attorney, Agent, or Firm* — Venable LLP; Henry J. Daley

(57) ABSTRACT

Electrochemical and bio sensors using metal oxide semiconductors and method of making the same are described herein. The sensor includes a gate electrode, a dielectric layer over the gate electrode, a channel layer over the dielectric layer, and source and drain electrodes formed on the channel layer to provide a field effect transistor structure. The channel layer is a metal oxide semiconductor film that has a substantially uniform thickness of at least 3 nm thick and less than 10 nm thick. The metal oxide semiconductor film is functionalized with molecules attached thereto that are open to make contact with a fluid for detection of at least one component or at least one physical or chemical property of the fluid.

17 Claims, 17 Drawing Sheets

(51) Int. Cl.
  *G01N 33/543* (2006.01)
  *G01N 33/552* (2006.01)
  *A61B 5/1468* (2006.01)
  *C12Q 1/00* (2006.01)

(52) U.S. Cl.
  CPC ..... *G01N 27/4071* (2013.01); *G01N 27/4145* (2013.01); *G01N 33/5438* (2013.01); *G01N 33/552* (2013.01)

(56) References Cited

U.S. PATENT DOCUMENTS

| | | | |
|---|---|---|---|
| 9,412,852 B2* | 8/2016 | Facchetti | C23C 18/1216 |
| 9,779,938 B2* | 10/2017 | Takata | H01L 21/02554 |
| 2015/0087110 A1* | 3/2015 | Facchetti | H01L 21/02381 |
| | | | 438/104 |

OTHER PUBLICATIONS

Badugu et al., "Ophthalmic Glucose Sensing: A Novel Monosaccharide Sensing Disposable and Colorless Contact Lens," Analyst 2004, 129, pp. 516-521.
Chaudhury et al., "Direct Measurement of Interfacial Interactions between Semispherical Lenses and Flat Sheets of Poly(dimethylsiloxane) and Their Chemical Derivatives," Langmuir 1991, 7, pp. 1013-1025.
Chen et al., "Low-Impurity High Performance Solution-Processed Metal Oxide Semiconductors via a Facile Redox Reaction.Pdf>," Chem. Mater. 2015, 27, pp. 4713-4718.
Chen et al., "Silicon Nanowire Field-Effect Transistor-Based Biosensors for Biomedical Diagnosis and Cellular Recording Investigation," Nano Today 2011, 6, pp. 131-154.
Cheng et al., "Mechanism and Optimization of Ph Sensing Using SnO2 Nanobelt Field Effect Transistors," Nano Lett. 2008, 8, pp. 4179-4184.
Choi et al., "Stretchable Heater Using Ligand-Exchanged Silver Nanowire Nanocomposite for Wearable Articular Thermotherapy," ACS Nano 2015, 9, pp. 6626-6633.
Claussen et al., "Nanostructuring Platinum Nanoparticles on Multilayered Graphene Petal Nanosheets for Electrochemical Biosensing," Adv. Funct. Mater. 2012, 22, pp. 3399-3405.
Cui et al., "Nanowire Nanosensors for Highly Sensitive and Selective Detection of Biological and Chemical Species," Science 2001, 293, pp. 1289-1292.
Daum et al. "Human Tear Glucose," Invest. Ophthalmol. Vis. Sci. 1982, 22, pp. 509-514.
Dzyadevych et al., "Enzyme Biosensors Based on Ion-Selective Field-Effect Transistors," Anal. Chim. Acta. 2006, 568, pp. 248-258.
Ha et al., "Triboelectric Generators and Sensors for Self-Powered Wearable Electronics," ACS Nano 2015, 9, pp. 3421-3427.
Hammock et al., "25th Anniversary Article: The Evolution of Electronic Skin (E-Skin): A Brief History, Design considerations, and Recent Progress," Adv Mater 2013, 25, pp. 5997-6038.
Huang et al., "Epidermal Differential Impedance Sensor for Conformal Skin Hydration Monitoring," Biointerphases 2012, 7.
Kim et al., "Dissolvable Films of Silk Fibroin for Ultrathin Conformal Bio-Integrated Electronics," Nature Mater. 2010, 9, pp. 511-517.
Kim et al., "Epidermal Electronics," Science 2011, 333, pp. 838-843.
Kim et al., "Fabrication of High-Performance Ultrathin In2o3 Film Field-Effect Transistors and Biosensors Using chemical Lift-Off Lithography," ACS Nano 2015, 9, pp. 4572-4582.
Kim et al., "Highly Sensitive and Multimodal All-Carbon Skin Sensors Capable of Simultaneously Detecting Tactile and Biological Stimuli," Adv. Mater. 2015, 27, 4105.
Kuila et al., "Recent Advances in Graphene-Based Biosensors," Biosens. Bioelectron. 2011, 26, pp. 4637-4648.
Li et al., "Chemical Gating of In2o3 Nanowires by Organic and Biomolecules," Appl. Phys. Lett. 2003, 83, pp. 4014-4016.
Maheshwari et al., "High-Resolution Thin-Film Device to Sense Texture by Touch," Science 2006, 312, pp. 1501-1504.
Mannsfeld et al., "Highly Sensitive Flexible Pressure Sensors with Microstructured Rubber Dielectric Layers," Nature Mater. 2010, 9, pp. 859-864.
Neithercott, "14 "Next Big Thing" Diabetes Care Products", Diabetes Forecast 2015, 68, pp. 33-35.
Park et al., "Graphene-Based Conformal Devices," ACS Nano 2014, 8, pp. 7655-7662.
Porchetta et al., "General Strategy to Introduce Ph-Induced Allostery in DNA-Based Receptors to Achieve Controlled Release of Ligands," Nano Lett. 2015, 15, pp. 4467-4471.
Rim et al., "Boost up Mobility of Solution-Processed Metal Oxide Thin-Film Transistors via Confining Structure on Electron Pathways," Adv. Mater 2014, 26, pp. 4273-4278.
Rim et al., "Direct Light Pattern Integration of Low-Temperature Solution-Processed All-Oxide Flexible Electronics," ACS Nano 2014, 8, pp. 9680-9686.
Rim et al., "Simultaneous Modification of Pyrolysis and Densification for Low-Temperature Solution-Processed Flexible oxide Thin-Film Transistors," J. Mater. Chem. 2012, 22, pp. 25492-25492.
Rogers et al., "Materials and Mechanics for Stretchable Electronics," Science 2010, 327, pp. 1603-1607.
Roh et al., "Stretchable, Transparent, Ultrasensitive, and Patchable Strain Sensor for Human-Machine Interfaces Comprising a Nanohybrid of Carbon Nanotubes and Conductive Elastomers," ACS Nano 2015, 9, pp. 6252-6261.
Ryu et al., "Extremely Elastic Wearable Carbon Nanotube Fiber Strain Sensor for Monitoring of Human Motion," ACS Nano 2015, 9, pp. 5929-5936.
Sarkar et al., "Correction to MoS2, Field-Effect Transistor for Next-Generation Label-Free Biosensors," ACS Nano 2014, 8, pp. 5367-5367.
Sarkar et al., "Most, Field-Effect Transistor for Next-Generation Label-Free Biosensors," ACS Nano 2014, 8, pp. 3992-4003.
Sekitani et al., "A Rubberlike Stretchable Active Matrix Using Elastic Conductors," Science 2008, 321, pp. 1468-1472.
Seung et al., "Nanopatterned Textile-Based Wearable Triboelectric Nanogenerator," ACS Nano 2015, 9, pp. 3501-3509.
Someya et al., "A Large-Area, Flexible Pressure Sensor Matrix with Organic Field-Effect Transistors for Artificial Skin Applications," Proc. Natl. Acad. Sci. U.S.A. 2004, 101, pp. 9966-9970.
Someya et al., "Conformable, Flexible, Large-Area Networks of Pressure and Thermal Sensors with Organic Transistor Active Matrixes.," Proc. Natl. Acad. Sci. U.S.A. 2005, 102, pp. 12321-12325.
Sun et al., "A Review of Carbon Nanotube- and Graphene-Based Flexible Thin-Film Transistors," Small 2013, 9, pp. 1188-1205.
Takahashi et al., "Carbon Nanotube Active-Matrix Backplanes for Conformal Electronics and Sensors," Nano Lett. 2011, 11, pp. 5408-5413.
Takei et al., "Nanowire Active-Matrix Circuitry for Low-Voltage Macroscale Artificial Skin," Nature Mater. 2010, 9, pp. 821-826.
Tian et al., "A Review of Recent Advances in Nonenzymatic Glucose Sensors," Mater. Sci. Eng. C Mater. Biol. Appl. 2014, 41, pp. 100-118.
Torsi et al., "Regioregular Polythiophene Field-Effect Transistors Employed as Chemical Sensors," Sensor Actual. B-Chem. 2003, 93, pp. 257-262.
Wang et al., "User-Interactive Electronic Skin for Instantaneous Pressure Visualization," Nature Mater. 2013, 12, pp. 899-904.
Wilson et al., "Glucose-Oxidase—An Ideal Enzyme," Biosens. Bioelectron. 1992, 7, pp. 165-185.
Windmiller et al., "Wearable Electrochemical Sensors and Biosensors: A Review," Electroanal. 2013, 25, pp. 29-46.
Xiang et al., "Using Personal Glucose Meters and Functional DNA Sensors to Quantify a Variety of Analytical Targets," Nature Chem. 2011, 3, pp. 697-703.

(56) References Cited

OTHER PUBLICATIONS

Zou et al., "Glucose Biosensor Based on Electrodeposition of Platinum Nanoparticles onto Carbon Nanotubes and Immobilizing Enzyme with Chitosan-SiO2 Sol-Gel," Biosens. Bioelectron. 2008, 23, pp. 1010-1016.

* cited by examiner

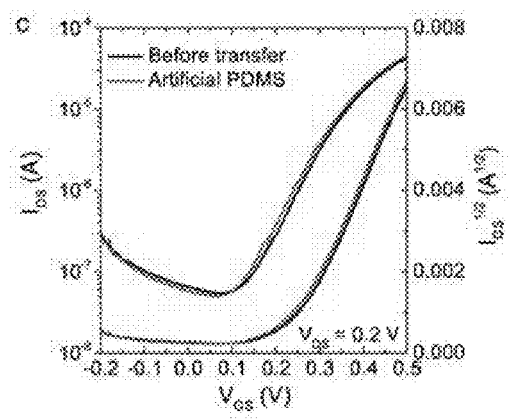
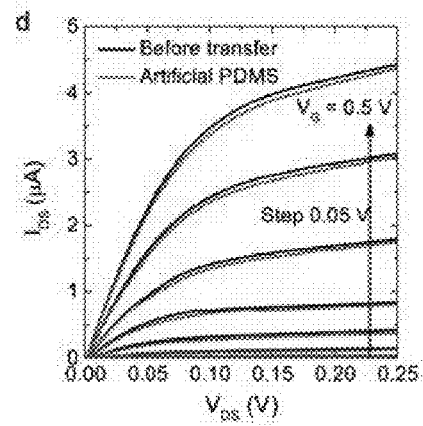
FIG. 5C    FIG. 5D
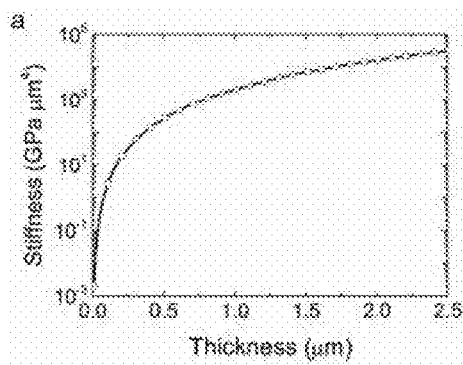
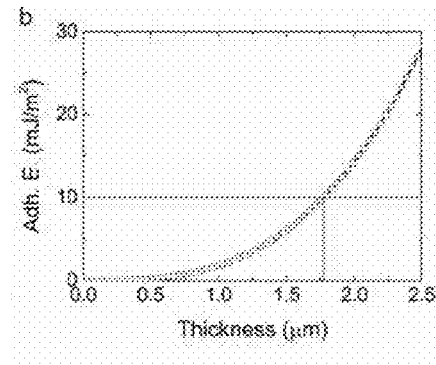
FIG. 6A    FIG. 6B

HIGH PERFORMANCE CHEMICAL AND BIO SENSORS USING METAL OXIDE SEMICONDUCTORS

CROSS-REFERENCE TO RELATED APPLICATIONS

This application claims priority benefit from U.S. Provisional Patent Application No. 62/380,809 filed on Aug. 29, 2016, and U.S. Provisional Patent Application No. 62/411,257 filed on Oct. 21, 2016, the entire content of both applications being incorporated herein by reference. All references cited anywhere in this specification, including the Background and Detailed Description sections, are incorporated by reference as if each had been individually incorporated.

BACKGROUND

1. Technical Field

The field of the currently claimed embodiments of this invention relates to chemical and bio sensors, and more particularly to chemical and bio sensors using metal oxide semiconductors.

2. Discussion of Related Art

The development of wearable sensors for in situ, rapid, and low-cost detection of various targets (e.g., heart rate and glucose levels) that are lightweight, comfortable, and small scale would be useful for many applications involving electronic skin, diagnosis, thermal regulation, and communication.[1-13] Depending on the specific applications, some types of nanomaterials including some nanowires, nanosheets, and nanoparticles made of inorganic or organic materials have been used because of their high sensitivity and flexibility.[3,14-23] Considering the functional nanostructures of biosensors, the selection of the detection platform plays a role in high sensitivity and reproducibility, including low detection limits, low device-to-device variation, real-time detection, and simple integration with wearable environments (e.g., human skin, clothes, and flexible or rollable electronic devices). Field-effect transistor (FET)-based biosensors are well suited to detecting biomolecules because the exposed semiconductor channel regions can be chemically modified with high sensitivity functional groups or receptors.[24-27] Specific interactions between receptor groups and their targets alter local electric fields causing variations in channel conductance even at relatively low target concentrations. This control can be due to conformational changes upon recognition in the receptors that are held close to the active element or by displacing environmental charges with neutral, less charged, or oppositely charged components of the receptors.[26] One-dimensional (1D) and two-dimensional (2D) nanomaterials such as Si nanowires (SiNWs), carbon nanotubes (CNTs), graphene, and $In_2O_3$ or $MoS_2$ thin-films have been employed as channel materials for FET platforms because of their large surface-to-volume ratios and similar electric potentials of the surface and bulk, thus providing high sensitivity and response.[25,26,28-31]

The major challenges of using nanomaterials for FET-based wearable biosensors are obtaining both the required conformality and reproducibility with simple processing.[4,10,17] Achieving highly conformal contact of devices on curvilinear, complex surface topologies of biological tissues, skin, electronic devices, and unknown targets is also one goal.[1] Several approaches have been taken to address issues associated with curvilinear and/or irregular surfaces such as using silk fibroin or ultrathin polyethylene terephthalate (PET), and transferring devices by an exfoliating method.[7,20-22,32] Reproducibility is highly related to the material systems, including 1D and 2D growth and integration on devices, and is essential to controlling densities and alignment to obtain electrical uniformity through complex processing.

Although these approaches have been significantly improved for developing conformal and highly sensitive devices, complex processing and materials have been considered because of easy deterioration and reproducibility. Therefore, there remains a need for improved chemical and bio sensors and in particular a need remains for chemical and bio sensors that are wearable and conform to contours and topologies of biological tissues, skin and other target materials as well as sensor that are capable of detecting target chemicals such as glucose.

SUMMARY OF THE DISCLOSURE

An aspect of the present disclosure is to provide a method of producing a metal oxide semiconductor film for sensor devices. The method includes mixing at least one of a metal nitrate or a hydrate of a metal nitrate precursor in a solvent to obtain a precursor solution; depositing a layer of the precursor solution onto a surface of a substrate; and annealing the layer of the precursor solution to provide the metal oxide semiconductor film. The metal oxide semiconductor film has a substantially uniform thickness of at least 3 nm thick and less than 10 nm thick.

Another aspect of the present disclosure is to provide an electrochemical sensor, comprising: a gate electrode; a dielectric layer over the gate electrode; a channel layer over the dielectric layer; and source and drain electrodes formed on the channel layer to provide a field effect transistor structure. The channel layer is a metal oxide semiconductor film that has a substantially uniform thickness of at least 3 nm thick and less than 10 nm thick. The metal oxide semiconductor film is functionalized with molecules attached thereto that are open to make contact with a fluid for detection of at least one component or at least one physical or chemical property of the fluid.

A further aspect of the present disclosure is to provide an electronic sensor, comprising: a gate electrode; a dielectric layer over the gate electrode; a metal-oxide semiconductor channel layer over the dielectric layer; source and drain electrodes formed on the channel layer to provide a field effect transistor structure. The electronic sensor further comprises a silane functionalization layer formed on the metal-oxide semiconductor layer; and a receptor layer formed on the silane functionalization layer. The receptor layer is open to receive molecules of a species to be detected.

Another aspect of the present disclosure is to provide s method of producing an electronic sensor. The method includes receiving a thin film field effect transistor having a metal-oxide channel layer and a silane functionalization layer on the metal-oxide channel layer; and forming a receptor layer on the silane functionalization layer.

BRIEF DESCRIPTION OF THE DRAWINGS

The present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

FIGS. 5C and 5D show plots of current versus voltage showing the performance of liquid-gated $In_2O_3$ FETs on rigid and skin-replica PDMS, according to an embodiment of the present disclosure;

FIG. 6A shows a plot of stiffness versus thickness of the conformal contact of thin-film $In_2O_3$ FET devices on artificial polydimethylsiloxane (PDMS) skin, according to an embodiment of the present disclosure;

FIG. 6B is a plot of the adhesion energy versus the thickness of the thin-film $In_2O_3$ FET device, according to an embodiment of the present disclosure;

DETAILED DESCRIPTION

Figure 1:
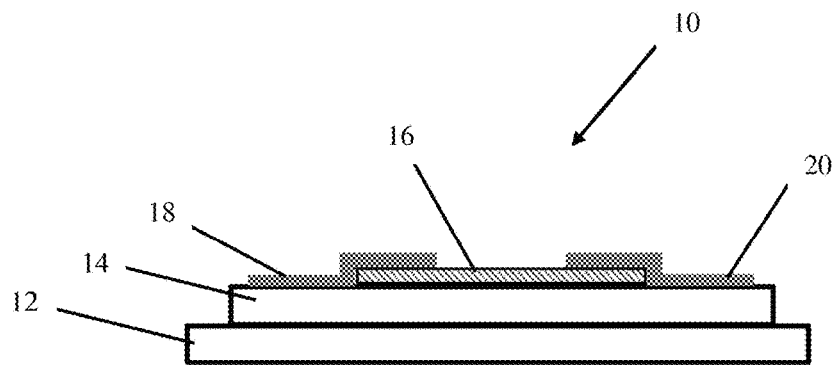
FIG. 1 is a schematic representation of an electrochemical sensor, according to an embodiment of the present disclosure.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

According to an embodiment of the present disclosure, there is provided a solution-processed metal oxide semiconductors via a chemistry with a low impurity to fabricate ultrathin films. In an embodiment, spin-coating of indium oxide solution formed ultrathin film (~3.5 nm) with high film density method is used. Ultrathin films can avoid the intrinsic effect of strain such as the physical strain and the peeling behavior from the substrate. Furthermore, oxide surface is highly feasible to employ chemical functionalization for the biological moieties. In an embodiment, highly sensitive, conformal biosensors can be produced using the above method. The biosensors can be used for non-invasive health monitoring and are wearable. In some embodiments, for example, the biosensors can be used to measure pH and glucose levels. The pH levels in the human body can change in response to physiologic conditions such as tumorigenesis.' Local pH values not only provide important information for drug delivery but also reflect health problems directly.' Moreover, blood glucose levels are altered in patients with diabetes mellitus. Currently, regular monitoring requires the use of invasive finger-stick tests to determine blood glucose levels.' A non-invasive test for glucose levels in tears is challenging to develop because of the need for glucose detection limits in the range of 0.1-0.6 mM, which is lower than glucose concentrations in blood (2-30 mM in diabetics).[37-39]

Therefore, as it can be further understood in the following paragraphs, some embodiments of the present disclosure are directed to novel nano film based sensors that have compatibility to be worn and are flexible for applications that can include bio medical applications, such as measuring and/or monitoring blood glucose levels, pH levels or other bio function chemical or enzyme. For example, specially designed metal nitrate precursor-based ultrathin indium oxide films (having a thickness of ~3.5 nm) at low temperature (about 250° C.) have high potential for eco-friendly and low cost processing for sensor fabrication. Furthermore, the present novel system-based sensors can easily adapt to a rough surface and skin to achieve wearable sensors. Some embodiments of the current disclosure can be applicable to wearable electronics and bio-medical sensor applications. Some commercial applications can include, but are not limited to, disease diagnosis and bio detection for wearable electronics and medical applications. For example, in comparison with conventional glucose sensors, the present novel sensor system described herein can be applied to non-invasive test for glucose levels using saliva or tears. In addition, the present sensors can be applied to flexible electronics with wearable sensors. The large area processing of the sensors can be also applied to roll-to-roll mass production for low cost process.

Therefore, in an embodiment, there is provided a method of producing a metal oxide semiconductor film for sensor devices. The method includes mixing at least one of a metal nitrate or a hydrate of a metal nitrate precursor in a solvent to obtain a precursor solution. The method further includes depositing a layer of the precursor solution onto a surface of a substrate. The layer of the precursor solution is then annealed to provide or obtain a metal oxide semiconductor film. The metal oxide semiconductor film has a substantially uniform thickness of at least 3 nm thick and less than 10 nm thick.

In an embodiment, the metal oxide semiconductor film is a substantially amorphous film. In an embodiment, the metal oxide semiconductor film has a substantially uniform thickness that is uniform to within a root-mean-square deviation of less than 10%. In an embodiment, the substantially uniform thickness of the metal oxide film is uniform to within a root-mean-square deviation of less than 30%. In an embodiment, the metal oxide semiconductor film has a substantially uniform thickness of at least 1 nm thick and less than 5 nm thick. In an embodiment, the metal oxide semiconductor film has a substantially uniform thickness of about 3.5 nm thick. In an embodiment, the metal nitrate or the hydrate of the metal nitrate precursor is mixed in water (for example deionized water) which acts as the solvent. In an embodiment, the metal nitrate or the hydrate of the metal nitrate precursor is indium nitrate hydrate. In an embodiment, the metal nitrate or the hydrate of the metal nitrate precursor is at least one of indium nitrate hydrate, zinc nitrate hydrate, aluminum nitrate hexahydrate, gallium nitrate hydrate, or titanium nitrate.

In an embodiment, the precursor solution has a concentration of the metal nitrate or the hydrate of the metal nitrate precursor within a range of 0.05 mole to 0.1 mole in solution. In an embodiment, the annealing includes a pre-baking procedure to remove solvent from the layer of the precursor solution after the depositing of the layer of the precursor solution onto the surface of the substrate. In an embodiment, the annealing procedure includes a hard-baking of the layer to form an oxide film. In an embodiment, the pre-baking is performed at about 100° C. and the hard-baking is performed at about 250° C.

In an embodiment, the substrate is a flexible substrate. In an embodiment, the substrate is at least one of a glass substrate, a silicon substrate, polymer substrate, and metal substrate. In an embodiment, the substrate has a thickness of at least 0.5 μm and less than 2 μm.

In an embodiment, there is provided an electrochemical sensor 10. FIG. 1 is schematic representation of the electrochemical sensor 10, according to an embodiment of the present disclosure. The electrochemical sensor 10 includes a gate electrode 12. The sensor 10 further includes a dielectric layer 14 (e.g., silicon oxide $SiO_2$) over the gate electrode 12, and a channel layer 16 over the dielectric layer 14. The sensor 10 also includes source and drain electrodes 18 and 20 formed on the channel layer 16 to provide a field effect transistor structure. The channel layer 16 is a metal oxide semiconductor film that has a substantially uniform thickness of at least 3 nm thick and less than 10 nm thick. The metal oxide semiconductor film of the channel layer 16 is functionalized with molecules attached thereto that are open to make contact with a fluid for detection of at least one component or at least one physical or chemical property of the fluid. In an embodiment, the metal oxide semiconductor film of the channel layer 16 is produced according to the method described in the above paragraphs. In an embodiment, the metal oxide semiconductor film of the channel layer 16 has a substantially uniform thickness of about 3.5 nm thick. The term "about 3.5 nm thick" means that it can deviate from that value within the manufacturing precision of processes described in this specification and/or others used in the future and/or as otherwise required by a particular application.

In an embodiment, the metal oxide semiconductor film of the channel layer 16 is functionalized with at least one type of enzyme immobilized on a surface of the metal oxide semiconductor film. In an embodiment, at least one type of enzyme immobilized on a surface of the metal oxide semiconductor film of the channel layer 16 is a glucose oxidase so as to form an electrochemical glucose sensor 10 configured to detect glucose. In another embodiment, the metal oxide semiconductor film is functionalized with a salinized (3-Aminopropyl)triethoxysilane (APTES) such that the electrochemical sensor 10 is a pH sensor. In an embodiment, the metal oxide semiconductor film includes an indium oxide ($In_2O_3$) film.

Some examples of manufacturing methods and examples of produced electrochemical sensors are further described in the following paragraphs. In an embodiment, an ultrathin (with a thickness of about 3.5 nm or approximately 4 nm) and highly uniform indium oxide ($In_2O_3$) semiconductors is produced via a single spin-coating step using hexaaqua metal (III) complexes and annealing at low temperature (250° C.). Oxide semiconductors that are a few nanometers thick have high surface sensitivities and reactivities with specific molecular assemblies that are advantageous for detecting specific analytes. Simple and fast removal of conformal films from underlying substrates are well suited to wearable biosensor applications. The obtained ultrathin $In_2O_3$ semiconductors are mechanically stable following removal from substrates. By combining ultrathin $In_2O_3$ semiconductor-based FETs with conformal films, biosensors that are highly sensitive, easily processed, economical, and conformal that detected pH values and glucose concentrations with physiologically relevant detection limits are produced.

Figure 2A:
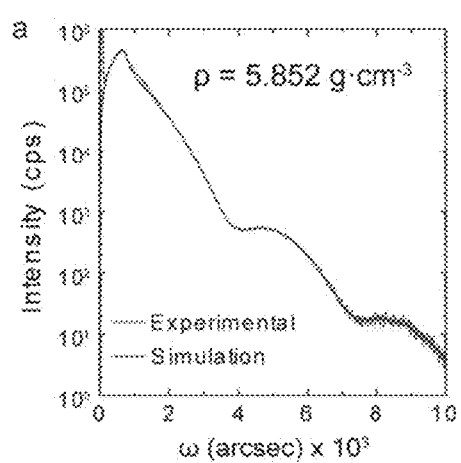
FIG. 2A is a graph of X-ray reflectivity of an $In_2O_3$ thin-film, according to an embodiment of the present disclosure.
Figure 2B:
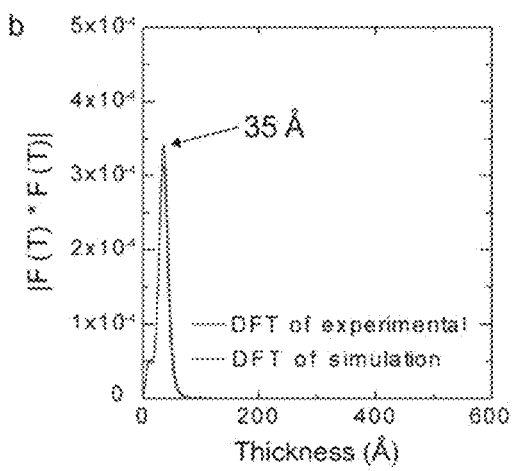
FIG. 2B is a graph of a discrete Fourier-Transform (DFT) versus thickness of the film providing a comparison between a simulation and an experimental measurement, according to an embodiment of the present disclosure.

The $In_2O_3$ films are formed from an aqueous precursor. Resulting films have high densities, and are ultrathin and smooth. Film densities are measured by a non-destructive X-ray reflectivity measurement and simulation, which indicated a density of 5.852 g·cm$^{-3}$. FIG. 2A is graph of X-ray reflectivity of an $In_2O_3$ thin-film, according to an embodiment of the present disclosure. The film density, obtained from the X-ray reflectivity, is about 5.582 g·cm$^{-3}$, about 82% of the single crystal density of 7.12 g·cm$^{-3}$. Compared to single-crystal $In_2O_3$, the film had good density even after the 250° C. annealing process. Spin-coating of $In_2O_3$ solutions formed 35-Å-thick films, which were verified by Discrete Fourier-Transform (DFT) simulation. FIG. 2B is a graph of a Discrete Fourier-Transform (DFT) versus thickness of the film providing a comparison between a simulation and the experimental measurement, according to an embodiment of the present disclosure. The DFT simulation was performed to obtain the precise thickness of $In_2O_3$ films (35 Å) based on XRR measurements. Furthermore, $In_2O_3$ films had smooth surfaces with a root-mean-square (RMS) roughness of 1.1 nm.

Figures 3A, 3B:
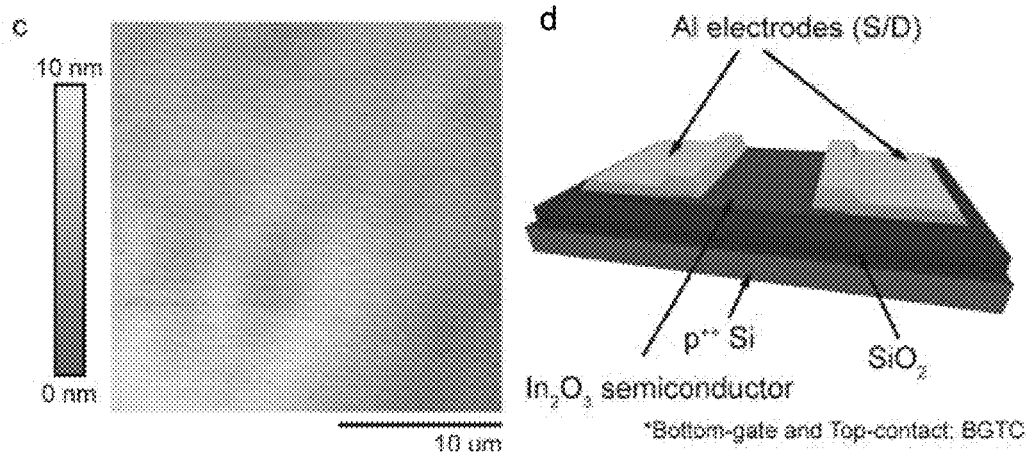
FIG. 3A is an atomic force microscope image of a 35-Å-thick $In_2O_3$ film, according to an embodiment of the present disclosure.
FIG. 3B is a perspective three-dimensional view of the device shown in FIG. 1, according to an embodiment of the present disclosure.
Figures 4A, 4B:
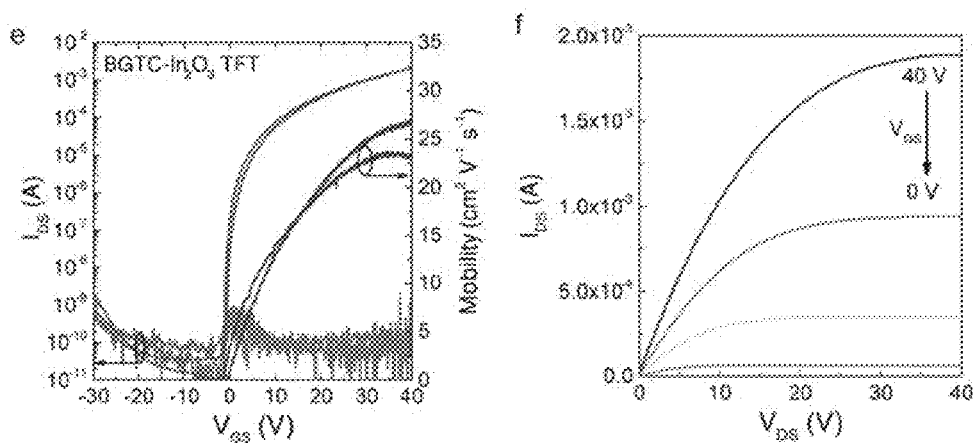
FIG. 4A shows a plot of current versus voltage and mobility versus voltage of the device shown in FIG. 1, according to an embodiment of the present disclosure.
FIG. 4B shows a plot of current versus gate drain voltage of the device shown in FIG. 1, according to an embodiment of the present disclosure.

FIG. 3A is an atomic force microscope image of a 35-Å-thick $In_2O_3$ film, according to an embodiment of the present disclosure. FIG. 3B is a perspective three-dimensional view of the device 10 shown in FIG. 1, according to an embodiment of the present disclosure. In an embodiment, the overall device structure shown in FIG. 3B is bottom-gate and top-contact (BGTC). Simple and facile processing of $In_2O_3$ semiconductor-based FETs is carried out. Typically, solution-processed metal-oxide FETs have poor electrical performance when fabricated via low-temperature processes. The devices produced here, however, showed high saturation mobilities ($\mu_{sat}$), large on/off ratios, and good switching behavior. It could be attributed to nitrate ligand-based the hexaaqua indium(III) cation ($[In(H_2O)_6]^{3+}$) is easily decomposed at low temperature and then formed high-density $In_2O_3$ films without organic residues compared to conventional methods. Hexaaqua indium(III) cation was very useful in the formulation to realize high performance $In_2O_3$ FETs. Saturation mobilities exceeded ~20 cm$^2$·V$^{-1}$·s$^{-1}$ with on/off ratios over $10^7$. The gate-to-source leakage current ($I_{GS}$, gray line) was below 100 pA. FIG. 4A shows a plot of the current versus voltage and mobility versus voltage of the device 10, according to an embodiment of the present disclosure. FIG. 4B shows a plot of the current versus gate drain voltage in the device 10, according to an embodiment of the present disclosure. Output curves of $In_2O_3$ FETs induced gate voltages between 0-40 V. The BGTC-$In_2O_3$ FETs performed well with a $\mu_{sat}$ of 24.4±2.1 cm$^2$·V$^{-1}$·s$^{-1}$, $I_{on/off}$ of ~$10^8$, and sub-threshold voltage swing (S. S) of 0.58±0.1 V·dec$^{-1}$. Output curves showed good pinch-off behavior.

Figure 5A:
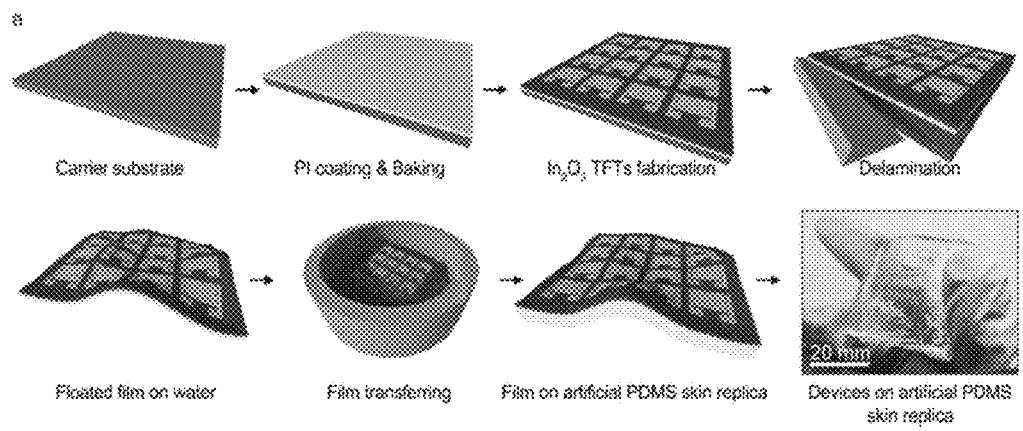
FIG. 5A illustrates schematically various steps in the fabrication of the electrochemical device shown in FIG. 1, according to an embodiment of the present disclosure.

FIG. 5A illustrates schematically various steps in the fabrication of the electrochemical device, according to an embodiment of the present disclosure. The ultrathin $In_2O_3$ FETs have good electrical performance after low-temperature processing. To realize pH-sensing and glucose-sensing using flexible transistor platforms, ultrathin polyimide (PI) films (2 μm) on glass substrates are fabricated followed by aqueous processing of $In_2O_3$ FETs with interdigitating electrodes. Interdigitated electrodes generate strong electric fields and show low current crowding effects. The fabricated devices are carefully delaminated under water and the hydrophobic PI films are stretched and floated in water. Finally, the devices are transferred onto artificial polydimethylsiloxane (PDMS) skin replicas having highly random surface structures. The ultrathin PI films conformably contacted the artificial skin surfaces via van der Waals forces. Conformal contacted devices on an artificial eye and on human skin are demonstrated.

Figure 5B:
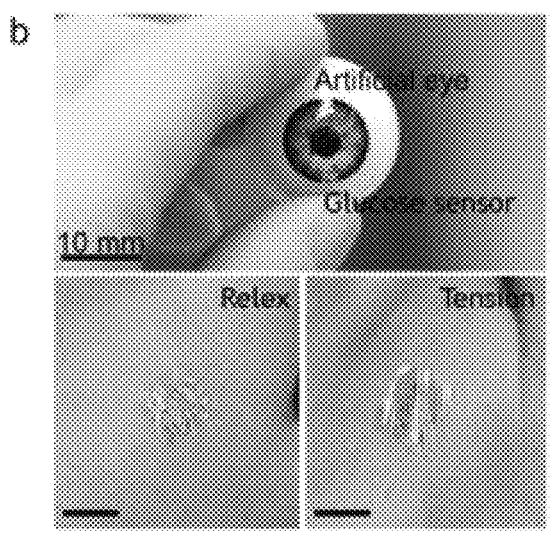
FIG. 5B depicts positioning of a conformal contacted devices on artificial eye and artificial skin surfaces, according to an embodiment of the present disclosure.

FIG. 5B depicts positioning of a conformal contacted devices on artificial eye and artificial skin surfaces, according to an embodiment of the present disclosure. The conformal contacted devices showed excellent mechanical behavior including flexibility, contact and tension. Glucose levels can be detected in tears, urine, saliva, and blood using the fabricated devices. However, tear glucose levels are lower than in blood and urine. To develop artificial contact lens glucose sensors, these differences in detection ranges need to be addressed (vide infra). Conformally contacted films exhibited good adhesion to skin, regardless of relaxation and tension of the hand.

Figure 8:
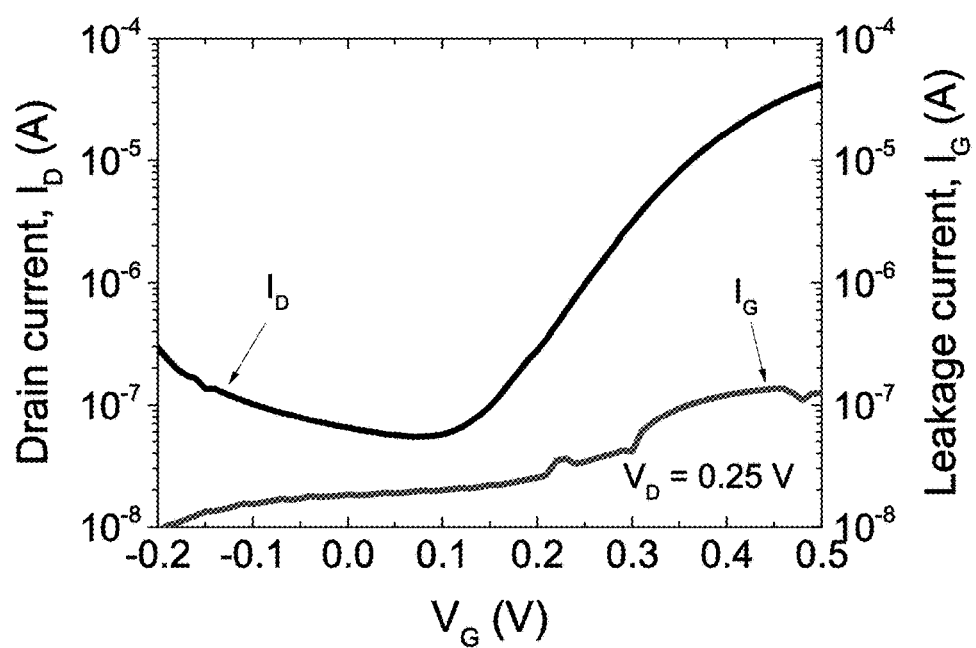
FIG. 8 shows transfer characteristics of liquid-gated $In_2O_3$ FETs, according to an embodiment of the present disclosure.
Figure 9:
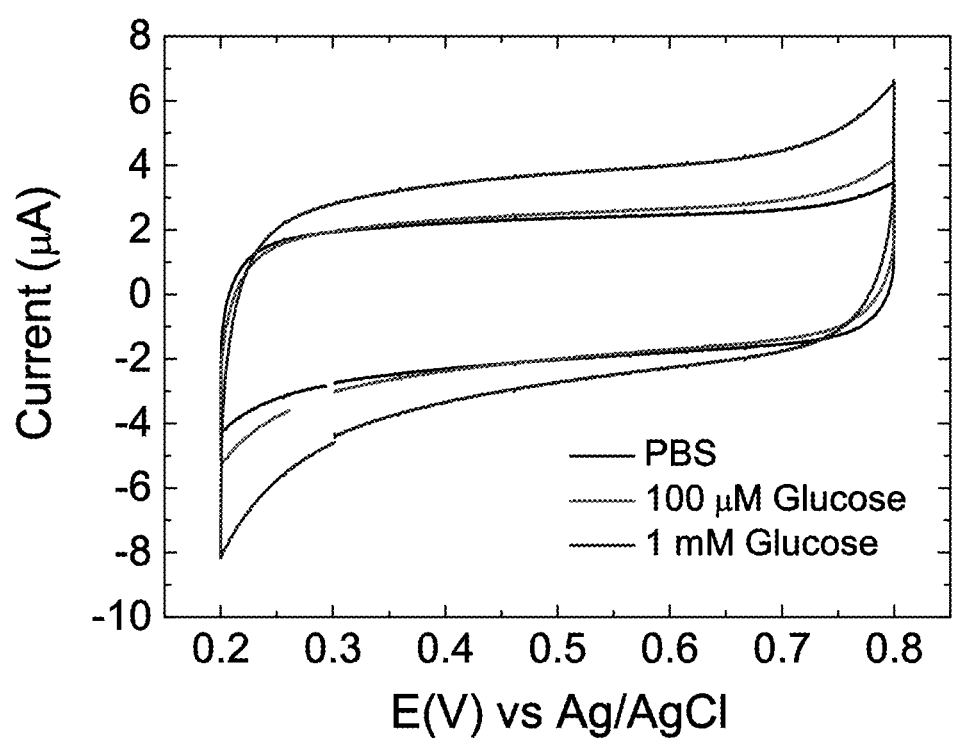
FIG. 9 shows cyclic voltammetry of a Pt foil in 0.1 M PBS with (blue: $C_G$=1 mM, red: $C_G$=100 μM or black: without) glucose, according to an embodiment of the present disclosure.

FIGS. 5C and 5D show plots of current versus voltage showing the performance of liquid-gated $In_2O_3$ FETs on rigid and skin-replica PDMS, according to an embodiment of the present disclosure. Ultrathin $In_2O_3$ deposited on thin PI films had small strain values when the devices are delaminated from glass substrates. Furthermore, the devices do not deteriorate on artificial PDMS skin samples with rough surfaces. The $In_2O_3$ FETs have good pinch-off behavior and low voltage driving with low leakage currents between the gold (Au) electrodes and the electrolyte. The latter avoids redox reactions between gate-source electrodes and target molecules in PBS solutions. FIG. 8 shows transfer characteristics of liquid-gated $In_2O_3$ FETs, according to an embodiment of the present disclosure. The transfer characteristics show that the leakage current between the liquid electrolyte ($I_G$) and the gate electrode is negligible. FIG. 9 shows cyclic voltammetry of a Pt foil in 0.1 M PBS with (blue: $C_G$=1 mM, red: $C_G$=100 μM or black: without) glucose, according to an embodiment of the present disclosure.

FIG. 6A shows a plot of stiffness versus thickness of the conformal contact of thin-film $In_2O_3$ FET devices on artificial polydimethylsiloxane (PDMS) skin, according to an embodiment of the present disclosure. For a more detailed analysis of conformal contact, adhesion energies between devices and target substrates are investigated. The critical adhesion energy for conformal contact was calculated enabling a prediction of the maximal device thickness that would enable conformal contact. FIG. 6B is a plot of the adhesion energy versus the thickness of the thin-film $In_2O_3$ FET device, according to an embodiment of the present disclosure. The intersection of the vertical and horizontal lines shows the maximal device thickness needed to make conformal contact with PDMS rough substrates.

Figure 6C:
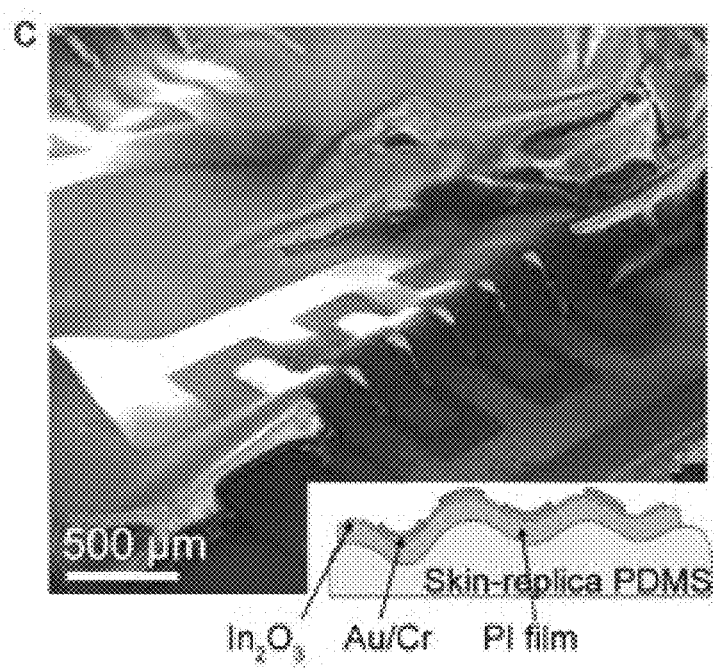
FIG. 6C is a scanning electron microscope (SEM) image of a representative device (thickness ~1.7 μm) on an artificial PDMS skin indicating conformal contact between the device and the substrate, according to an embodiment of the present disclosure.
Figure 10A:
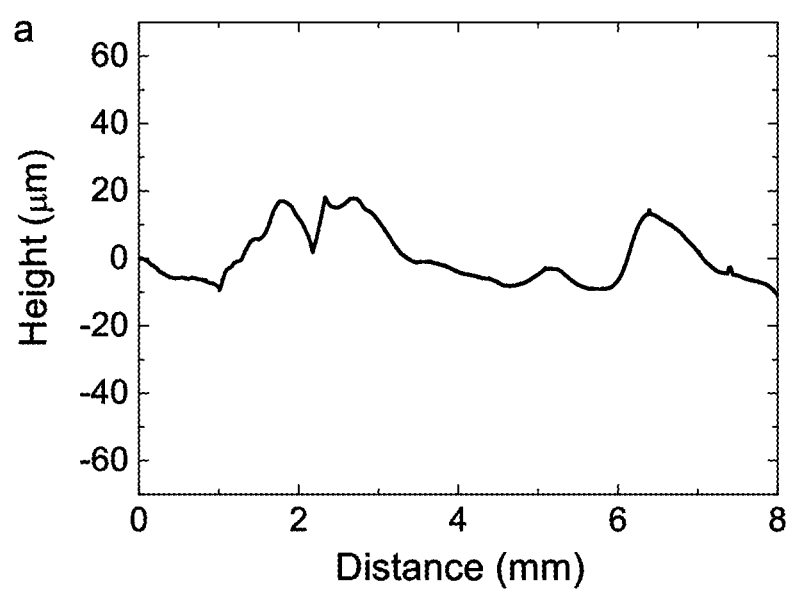
FIG. 10A depicts a surface profile information (height vs. distance) of the obtained device measured by using a surface profiler, according to an embodiment of the present disclosure.
Figure 10B:
FIG. 10B is a schematic illustration of a two-cylinder model used to calculate the adhesion energy between a device and a target surface, according to an embodiment of the present disclosure.

FIG. 10A depicts a surface profile information (height vs. distance) measured by using a surface profiler, according to an embodiment of the present disclosure. FIG. 10B is a schematic illustration of a two-cylinder model used to calculate the adhesion energy between a device and a target surface, according to an embodiment of the present disclosure. The surface roughness of target substrates is used to define the numerical model. Since the adhesion energy depends strongly on the bending stiffness of devices, stiffness is first calculated based on the mechanical properties of the devices and target substrates (see, FIG. 6A). Based on the calculated bending stiffness values, the relationship between adhesion energy and device thickness with respect to conformal contact is then investigated. Based on the surface profile, a two overlapping cylinder model for the numerical modeling of adhesion energy is derived. Since the required adhesion energy in a wet state for conformal contact is 10 mJ·m$^{-2}$, as described previously, the critical adhesion energy should be less than the required adhesion energy. Thus, the adhesion energy can be calculated using equation (1) below:

$$\gamma = \frac{EI}{2R^2 b}\{1 + (1+\lambda)R^2/(1-\lambda)r^2\}, \quad (1)$$

where $\gamma$, EI, R, b, $\lambda$, and r are the calculated adhesion energy, device stiffness, radius of the model cylinder, the width of the device, wavelength, and the arc between overlapped cylinders, respectively. Spontaneous and conformal contact begins to occur at a thickness of 1.77 µm, the critical device thickness (indicated in FIG. 6B by intersection point of the vertical and horizontal line), which indicates that conformal contact between the devices and the target substrates happens when each device has a thickness less than the critical thickness. FIG. 6C is Scanning electron microscope (SEM) image of a representative device (thickness ~1.7 µm) on an artificial PDMS skin indicating conformal contact between the device and the substrate, according to an embodiment of the present disclosure. FIG. 6C demonstrates successful conformal contact between the devices (thickness ~1.7 µm) and skin-replica PDMS.

Figure 7A:
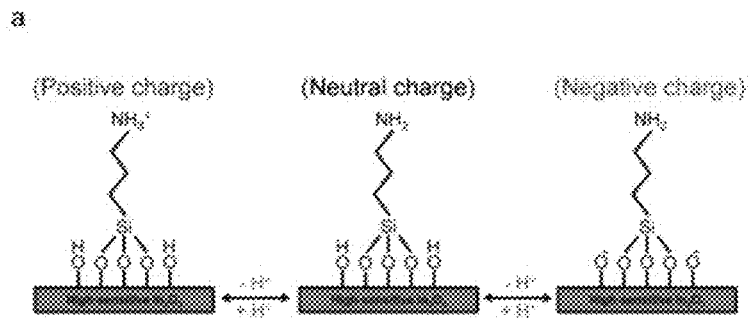
FIG. 7A shows a schematic for pH sensing using the ultrathin $In_2O_3$ FET-based biosensors developed here via a liquid gate set-up, according to an embodiment of the present disclosure.
Figure 7B:
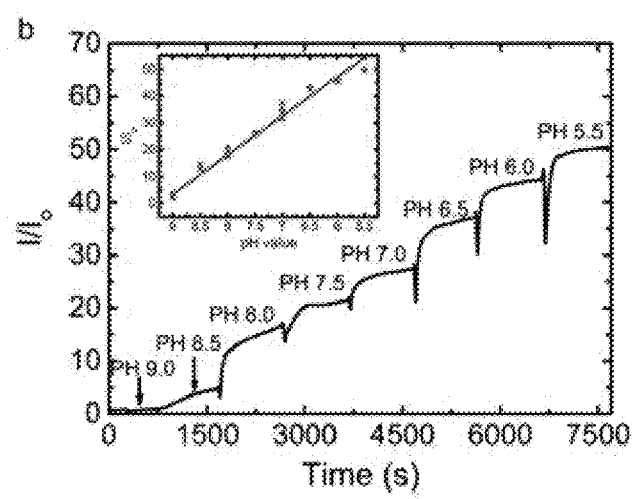
FIG. 7B shows a representative plot of the drain current response (PIO vs. pH shows that the response linearly decreases from pH 5.5 to pH 9.0, according to an embodiment of the present disclosure.

FIG. 7A shows a schematic for pH sensing using the ultrathin In$_2$O$_3$ FET-based biosensors developed here via a liquid gate set-up, according to an embodiment of the present disclosure. Prior to using FETs for pH sensing, In$_2$O$_3$ surfaces are silanized using amine-terminated (3-aminopropyl)triethoxysilane (APTES). FIG. 7B shows a representative plot of the drain current response (I/I$_o$) vs. pH shows that the response linearly decreases from pH 5.5 to pH 9.0, according to an embodiment of the present disclosure. The linear pH response occurred at a rate of 8.6±0.4 µA/pH unit originating from the deprotonation of APTES amine groups. The pH sensing mechanism occurs by protonation of In$_2$O$_3$ surface hydroxyl groups and primary amines of (3-aminopropyl)triethoxysilane (APTES) at decreasing pH (increasing proton concentrations).

Figure 11A:
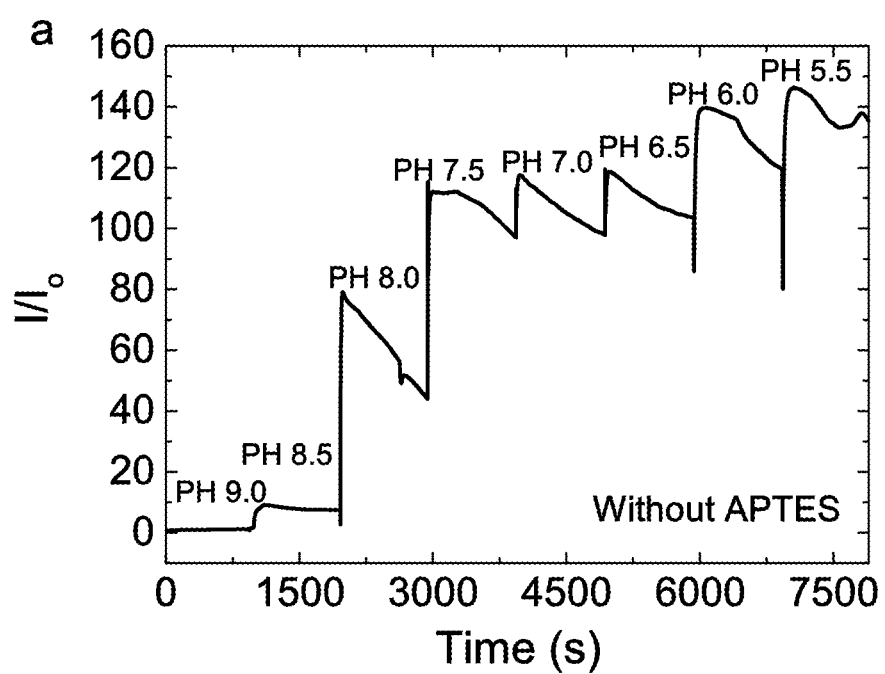
FIG. 11A shows a representative trace of the response of an $In_2O_3$ FET-based biosensor without APTES silanization as a function of pH, according to an embodiment of the present disclosure.
Figure 11B:
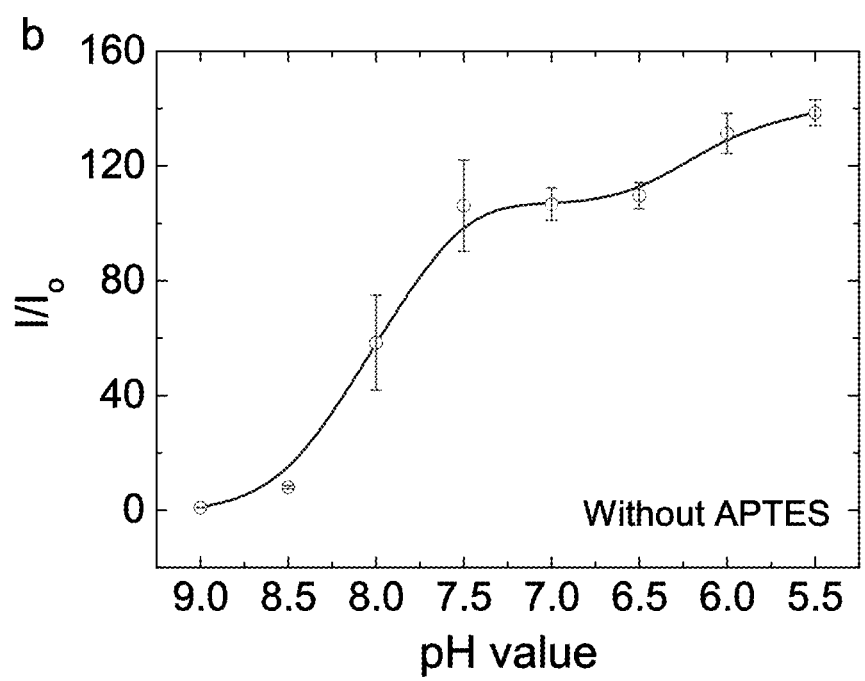
FIG. 11B shows a plot of average response values of these devices with respect to pH value of devices tested, according to an embodiment of the present disclosure.

FIG. 11A shows a representative trace of the response of an In$_2$O$_3$ FET-based biosensor without APTES silanization as a function of pH, according to an embodiment of the present disclosure. FIG. 11B shows a plot of average response values of these devices with respect to pH value of devices tested, according to an embodiment of the present disclosure. Error bars represent the standard deviations of the means. In an embodiment, the APTES-In$_2$O$_3$ surfaces have better pH sensitivity than unsilanized In$_2$O$_3$ FETs because amino groups were terminated on the surface of In$_2$O$_3$ films. Noise levels of devices without APTES are also higher than for devices with APTES. Moreover, unfunctionalized devices exhibited non-linear behavior over the pH range tested compared to devices with APTES silanization. In an embodiment, acquisition of positive charge due to protonation of surface amine groups alters local FET electric fields causing changes in conductance and thus, current. This behavior can be attributed to variations in surface charge densities. Typically, the proton Et concentration depends exponentially on pH values. It is predicted that current levels would similarly change exponentially for the present devices. Nonetheless, a linear response in pH variations can be observed. This linear response may be due to the compensation of surface charges with hydroxyl (—OH) and amine (—NH$_2$) functionalization.

Figure 7C:
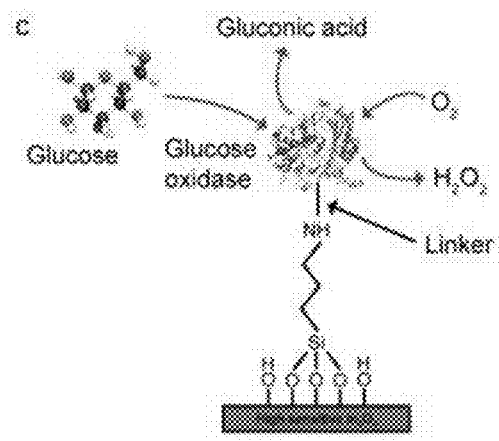
FIG. 7C depicts a schematic representation of glucose oxidase functionalized on $In_2O_3$ FET devices surfaces by covalent bonding to self-assembled APTES, according to an embodiment of the present disclosure.
Figure 7D:
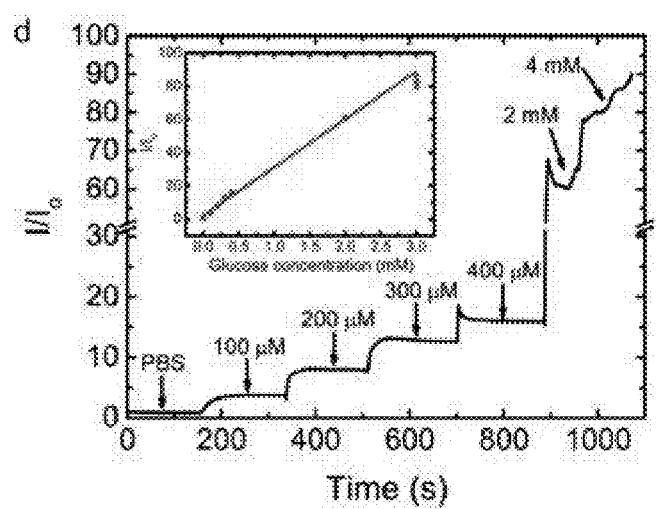
FIG. 7D shows representative responses from flexible $In_2O_3$ thin-film FET biosensors acquired upon addition of different glucose concentrations, according to an embodiment of the present disclosure.

FIG. 7C depicts a schematic representation of glucose oxidase functionalized on In$_2$O$_3$ FET devices surfaces by covalent bonding to self-assembled APTES, according to an embodiment of the present disclosure. Enzymatic oxidation of glucose results in the production of gluconic acid and hydrogen peroxide at the FET surfaces. To test the fabricated devices in a different chemical sensing application, In$_2$O$_3$-thin-film FET biosensors are used to detect glucose. Glucose sensing is based on oxidation of glucose by the enzyme glucose oxidase (GOx). Typically, previous glucose sensors are based on measuring changes in oxygen or H$_2$O$_2$ levels resulting from the enzymatic production of gluconic acid. FIG. 7D shows representative responses from flexible In$_2$O$_3$ thin-film FET biosensors acquired upon addition of different glucose concentrations, according to an embodiment of the present disclosure. As glucose was increased from 100 to 400 µM (the range expected in diabetic human tears), a linear current response was detected. Responses showed linear and saturating behavior. Moreover, higher concentrations of glucose such as those found in blood from diabetic individuals (i.e., 2 and 4 mM) can also be detected in with the same linear relationship as the lower glucose concentrations. Thus, the In$_2$O$_3$-based FET biosensors are compatible with a wide range of physiological glucose concentrations.

Aqueous Indium Oxide Precursor Solution.

In an embodiment, the indium oxide precursor solution is synthesized at a concentration of 0.2 M by dissolving 0.3 g of indium nitrate hydrate (In(NO$_3$)$_3$.xH$_2$O) in 5 mL of deionized water. After stirring vigorously for 1 h at 30° C., the solution appeared transparent.

Biosensor Fabrication.

In an embodiment, substrates are sequentially cleaned in acetone and isopropyl alcohol, and treated by ultraviolet (UV) irradiation for 10 min to remove organic residues and to improve solvent wettability. In an embodiment, the indium oxide precursor solution is spin-coated on SiO$_2$ (1000 Å)/heavily boron (B) doped p-type Si wafers or polyimide (PI)/glass substrates at 3000 rpm for 30 seconds. These samples are then soft-baked at 100° C. for 5 min to eliminate water and annealed at 250° C. for 3 h. To evaluate the electrical performance of In$_2$O$_3$ FETs, BGTC structure is used on Si wafers. The Au/Cr source and drain (S/D) electrodes (thickness=30/10 nm) are deposited by thermal evaporation through the shadow mask. The channel region is defined with a width (W) of 1000 µm and a length (L) of 200 µm. 20 pairs of In$_2$O$_3$ FETs were formed over an area of 1.5×1.5 cm. In an embodiment, interdigital electrodes (Au/Cr) are then formed using a standard photolithography process for the biosensor fabrication. In an embodiment, to prepare conformal substrate, a PI solution is spin-coated on glass substrates at 3000 rpm for 30 s. Samples are annealed in two steps: spin-coated substrates are pre-baked at 140° C. for 15 min (N$_2$ inert gas ambient) and annealed at 250° C. in air for 1 h. PI films were ~1.5 µm thick.

Chemical Treatment for Biosensing.

In an embodiment, for pH sensing, (3-aminopropyl)triethoxysilane (APTES) is self-assembled on indium oxide surfaces using 2% APTES by weight in toluene for 10 min. In an embodiment, samples are immediately cleaned using toluene. In another embodiment, for glucose sensing, two steps are added after silanization with APTES. A glutaraldehyde linker (GD) is added to the amino group of APTES using a solution of 2.5% GD in 0.1 M phosphate buffer solution (PBS) for 5 min. Samples are subsequently cleaned using 0.1 M PBS solution to remove physically adsorbed molecules. Finally, 2 mg of glucose oxidase (GO) from *Aspergillus niger* is immobilized via the GD linker in 1 mL 0.1 M PBS solution for 24 h.

Conformal Sensor Preparation and Mechanical Calculations.

In an embodiment, as-fabricated $In_2O_3$ semiconductors with interdigitated electrodes on PI are delaminated from the underlying glass substrates. Samples are placed in water and the sensor/PI films are carefully peeled from the glass substrates. The PI films are hydrophobic; hence, these films float in water. Finally, samples are transferred to test substrates with rough surfaces (i.e., artificial PDMS skin or an acrylic artificial eye). Theoretical calculations of adhesion energy, bending stiffness, and conformal contact thickness are detailed in supplementary section.

Characterization.

In an embodiment, X-ray reflectivity (XRR) measurements are performed using a Bede D1 diffractometer to calculate film densities and thicknesses. The morphology of the $In_2O_3$ films is investigated using atomic force microscopy (Dimension 5000 SPM, Veeco, now Bruker Nano, Santa Barbara, Calif.) and scanning electron microscopy (Nova 230, FEI, Hillsboro, Oreg.). In an embodiment, cyclic voltammetry is used to test the redox potential of glucose using a PAR EG&G 273A potentiostat with a Ag/AgCl reference electrode and a platinum-foil counter-electrode. The measurement is performed in 0.1 M PBS at a voltage sweep rate of 50 mV·s$^{-1}$ and a potential range of 0.2 to 0.8 V vs Ag/AgCl. In an embodiment, electrical measurements of FET-based sensors are performed using an Agilent 4155C semiconductor analyzer (Agilent Technologies, Inc., Santa Clara, Calif.).

Stiffness and Adhesion Energy Calculations for Determining Conformal Contact.

In an embodiment, to study the critical thickness to achieve conformal contact between the devices fabricated herein in accordance to some embodiments of the present disclosure and artificial PDMS rough substrates, which mimic human skin surface contours, stiffness calculations are performed. Stiffness values can be calculated using the following equation (2):

$$EI = EI_{PI} bh \left( \frac{1}{3} h^2 - h y_0 + y_0^2 \right) \quad (2)$$

where EI, b, h, and $y_0$ are overall device bending stiffness, device width, device thickness, and the distance between the neutral plane and bottom, respectively.

In an embodiment, the distance between the neutral plane and the bottom, $y_0$, is calculated using the following equation (3):

$$y_0 = \frac{h}{2} \times \frac{1 + \frac{2h' + h_m \left( \frac{E_{MO}}{E_{PI}} - 1 \right) \frac{n b_m h_m}{bh}}{h}}{1 + \left( \frac{E_{MO}}{E_{PI}} - 1 \right) \frac{n b_m h_m}{bh}} \quad (3)$$

where $E_{MO}$, $b_m$, and $h_m$ are the Young's modulus, and the width and height of the metal oxide layer, respectively.

In an embodiment, for the critical adhesion energy, a two-cylinder model based on the surface profile information is built (see, FIG. 10B). The total energy for the wrapped state is calculated by the following equation (4):

$$U_{total} = \frac{EI}{R} \left[ \frac{R\theta \sin\theta}{d - R\sin\theta} - \left( \frac{\gamma}{\gamma_c} - 1 \right) \left( \frac{L}{R} + \theta - \frac{d\theta}{R\sin\theta} \right) \right] \quad (4)$$

In an embodiment, the bending energy is calculated by the following equation (5):

$$U_{bending} = EI \frac{\theta \sin\theta}{d - R\sin\theta} + \frac{EI}{R^2} \left( L + R\theta - \frac{d\theta}{\sin\theta} \right) \quad (5)$$

In an embodiment, the adhesion energy is calculated by the following equation (6):

$$U_{adhesion} = -2\gamma b \left( L + R\theta - \frac{d\theta}{\sin\theta} \right) \quad (6)$$

wherein the contact angle of the device with one cylinder, θ, for the overlapped cylinder model can be expressed using equation (7):

$$\frac{R\sin\theta}{d - \sin\theta} + \frac{dR\theta\cos\theta}{(d - R\sin\theta)^2} - \left( \frac{\gamma}{\gamma_c} - 1 \right) \left( 1 - \frac{d}{R\sin\theta} + \frac{d\theta\cos\theta}{R\sin^2\theta} \right) = 0 \quad (7)$$

In an embodiment, the adhesion energy, expressed using equation (8), has a minimum value when θ=θ$_0$, wherein, R, $r_0$, d, E, and y, are 837 μm, 7.9 μm, 810 μm, 2.55 GPa, and 10 mJ/m$^2$ respectively.

$$\lambda = r_0 d / \{(R+r_0) \sqrt{(R+r_0)^2 - d^2} \sin^{-1}[d/(R+r_0)]\} \quad (8)$$

In an embodiment, based on the above information, three different cases for the contact condition can be defined. The first case, when γ is small, then $\gamma_c$ leads to non-conformal contact. The second case is partial conformal contact where γ is between $\gamma_c$ and $\gamma_c'$. The third case, once γ starts to become larger than $\gamma_c'$, complete conformal contact occurs where the relationship between $\gamma_c'$ and γ is provided by equations (9) and (10) as follows:

$$\gamma_c' = \gamma_c \{1 + (1+\lambda)R^2/(1-\lambda)r^2\} \quad (9)$$

$$\gamma \geq \gamma_c' = \frac{EI}{2R^2 b} \{1 + (1+\lambda)R^2/(1-\lambda)r^2\} \quad (10)$$

From the numerical modeling, the calculated critical thickness of the devices investigated here is 1.77 μm. Thus, these devices can begin to make conformal contact with the target surface at thicknesses <1.77 μm.

In the following paragraphs, examples of methods of fabrication of biosensors and biosensors are described. In an embodiment, a method includes synthesis of aqueous indium oxide precursor solution. In an embodiment, for example, the indium oxide precursor solution can be synthesized at a concentration of 0.2 M by dissolving 0.3 g of indium nitrate hydrate ($In(NO_3)_3 \cdot xH_2O$), respectively, in 5 mL of D.I. water ($H_2O$, Aldrich). After stirring vigorously for 1 hour at room temperature, the solution appeared transparent and homogeneous. Biosensors are then fabricated using the following process. In an embodiment, substrates are cleaned in acetone and isopropyl alcohol sequentially and then treated by ultraviolet (UV) irradiation for 10 min. The Indium oxide precursor solution is then spin-coated on the substrate. In an embodiment, the substrate can be $SiO_2$ (1000 Å) /heavily boron (B) doped p-type Si wafer or polyimide (PI)/glass substrate. In an embodiment, the spin coating is performed at 3000 rpm for 30 s. In an embodiment, the samples are soft-baked at 100° C. for 5 min to eliminate water and then annealed at 250° C. for 3 h. The annealed samples are patterned using a photolithography process. In an embodiment, to prepare a conformal substrate, the PI solution is spin-coated on glass substrates at 3000 rpm for 30 s. Then, substrates are annealed with two steps, sequentially. First, spin-coated substrates are pre-baked at 140° C. for 15 min ($N_2$ inert gas ambient) and are annealed at 250° C. in air for 1 hr. PI films are shown having a thickness of about 2 μm. The Au/Cr inter-digit electrodes (thickness=30/10 nm) are deposited by thermal evaporation and electrodes are formed with a lift-off process.

In an embodiment, pH and glucose sensors are fabricated using the following process. For example, for pH sensing, 3-Aminopropyl)triethoxysilane (APTES) is silanized on Indium oxide surface with 2 wt % APTES in toluene for 10 min and samples are cleaned using toluene. For glucose sensing, two steps are added after the silanization of APTES. Second, Glutaraldehyde linker (GD) is activated with the amino group of APTES, which is performed with 2.5% GD in 0.1 M PBS for 5 min. Samples are cleaned using 0.1 M PBS solution to remove physically adsorbed molecules. Third, glucose oxidate (GO) from *Aspergillus niger* is immobilized on GD linke with 2 mg GO in 1 ml 0.1 M PBS solution for 24 h. In an embodiment, delamination of conformal sensors is performed using the following procedure. As-fabricated sensors are able to delaminate from the glass substrate. Samples are needed to carry on water and films are carefully peeled-off from the glass substrate. PI film has hydrophobic surface so that the film is floated in water. Finally, samples are transferred in desired substrates with relatively high rough surfaces.

An embodiment of the present disclosure is directed to a method of functionalizing the channel of an oxide thin-film transistor, the method comprising: dissolving a chemical into a solvent to form solution, and immersing the device into the solution to functionalize the device.

In previous embodiments, a method of fabricating ultra-thin metal oxide thin-film transistors are described. A method is further provided of decorating gold electrode surface with 1-Dodecanethiol (DDSH) to prevent unintentional adsorption and the method of decorating oxide surface with (3-Aminopropyl)triethoxysilane (APTES) to protect the oxide surface. A sensor platform (device) can be obtained using the previous method(s). A selective detection of certain kind of molecule and/or ion can be achieved by decorating a specific kind of receptor on top of APTES.

Figure 12:
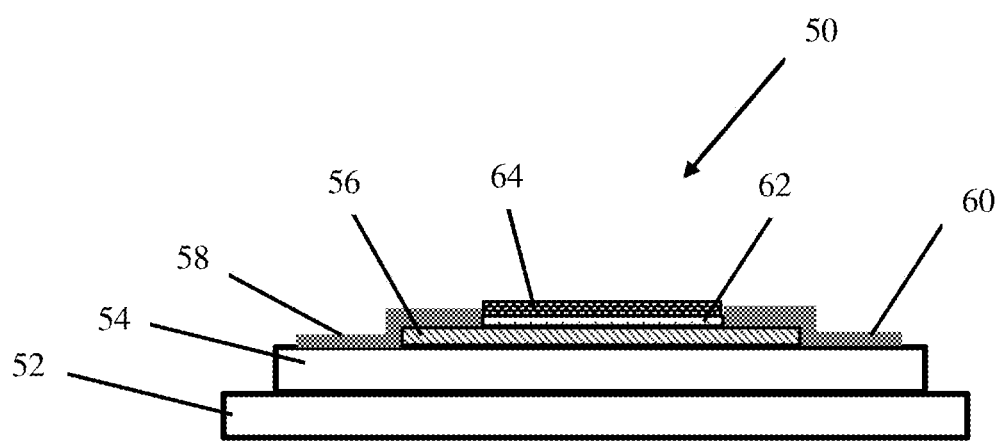
FIG. 12 is schematic representation of an electronic sensor configured to detect specific molecules, according to an embodiment of the present disclosure.

FIG. 12 is schematic representation of an electronic sensor 50 configured to detect specific molecules, according to an embodiment of the present disclosure. The sensor 50 includes a gate electrode 52, a dielectric layer 54 over the gate electrode 52, a metal-oxide semiconductor channel layer 56 over the dielectric layer 54, and a source and drain electrodes 58 and 60. The sensor 50 further includes a silane functionalization layer 62 formed on the metal-oxide semiconductor layer 56, and a receptor layer 64 formed on the silane functionalization layer 62. The receptor layer 64 is open to receive molecules of a species to be detected.

In an embodiment, the silane functionalization layer 62 is (3-Aminopropyl)triethoxysilane (APTES). In an embodiment, the receptor layer 64 includes a sublayer of glutaraldehyde (GA) formed on the silane functionalization layer 62 and a sublayer of 3-Aminophenylboronic acid monohydrate (APBA) formed on the sublayer of GA.

In an embodiment, the above sensor can be fabricated using the following method. The method includes receiving a thin film field effect transistor having a metal-oxide channel layer 56 and a silane functionalization layer 62 on the metal-oxide channel layer 56; and forming a receptor layer 64 on the silane functionalization layer 62. In an embodiment, the silane functionalization layer 62 is (3-Aminopropyl)triethoxysilane (APTES). In an embodiment, forming the receptor layer 64 comprises immersing the field effect transistor into a solution. In an embodiment, forming the receptor layer 64 comprises immersing the field effect transistor into a first solution for a first period of time and immersing the field effect transistor into a second solution for a second period of time. In an embodiment, immersing the field effect transistor into the first solution for the first period of time forms a sublayer of GA on the silane functionalization layer 62, and immersing the field effect transistor into the second solution for the second period of time forms a sublayer of APBA on the GA sublayer.

In an embodiment, in the case of fabricating a glucose sensor, the method includes dissolving 0.2~2 mL of 25% glutaraldehyde (GA) in 8 mL of phosphate-buffered saline (PBS) 1× solution. The method also includes immersing the device into GA solution for 24 hours. The method further includes taking out the device and rinsing the device with water, and blow drying the device with a nitrogen gun. In an embodiment, the method includes dissolving 0.1~1 g of 3-Aminophenylboronic acid monohydrate (APBA) and 0.0~40.4 g of Sodium cyanoborohydride ($NaBH_3CN$) into 10 mL PBS 1× solution. The method further includes immersing the device into APBA solution for 24 hours, taking out the device and rinse it with water, and blow drying the device with nitrogen gun.

Another embodiment is directed to a method of detecting chemicals using the sensor fabricated using the above method(s). The method of detecting a chemical or chemicals specific molecule attaching onto functionalized surface and changing the surface potential; detecting those molecules by monitoring the sensing current change at a given electrical bias. In an embodiment, in the case of glucose detection, the method includes dissolving different concentration of glucose into PBS 0.1× solution, and dropping 0.1×PBS solution onto a sensing surface. The method further includes measuring transistor transfer curve and determining the proper bias to compromise between sensitivity and stability. In an embodiment, the method may include time domain measurement, and waiting a period of time until the reading is stabilized and determining the baseline. The method further includes dropping or depositing glucose solution onto the sensing surface and recording the change in sensing current. In an embodiment, the sensing current is stabilized after the sensor adapts to the chemical environment (0.1×PBS solution) and current decreases 18% after adding 2 of 3 pM glucose solution into 50 μL of 0.1×PBS solution baseline.

Figure 13:
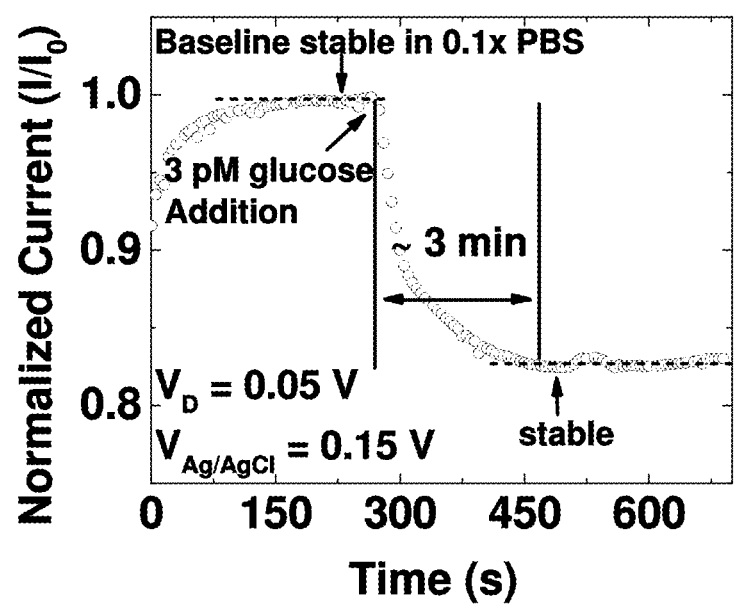
FIG. 13 is a plot of a normalized current as function of time showing a decrease in current in the device upon addition of glucose, according to an embodiment of the present disclosure.

FIG. 13 is a plot of a normalized current as function of time showing a decrease in current upon addition of glucose, according to an embodiment of the present disclosure. The sensor shows consistent shifting in transfer curve when adding more and more glucose into the solution.

Figure 14:
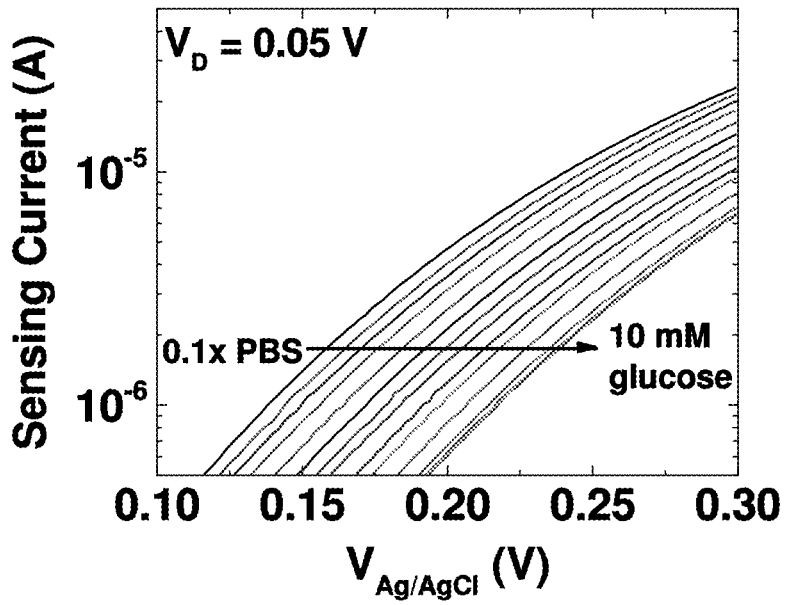
FIG. 14 is a plot of sensing current versus voltage in the device at various concentration of glucose, according to an embodiment of the present disclosure.

FIG. 14 is a plot of sensing current versus voltage in the sensor device at various concentration of glucose, according to an embodiment of the present disclosure. As shown in FIG. 14, the detection limit is below 0.1 pM and the linear detection range is between 10 pM and 10 μM. Within the linear range, the sensing current increases by 22% when the glucose concentration decreases by one decade. Compared with commercialized electrochemical glucose sensors, the present glucose sensor has much lower detection limit. In addition, when compared with other non-enzymatic electronic detection methods, the present glucose sensor has higher sensitivity.

Figure 15:
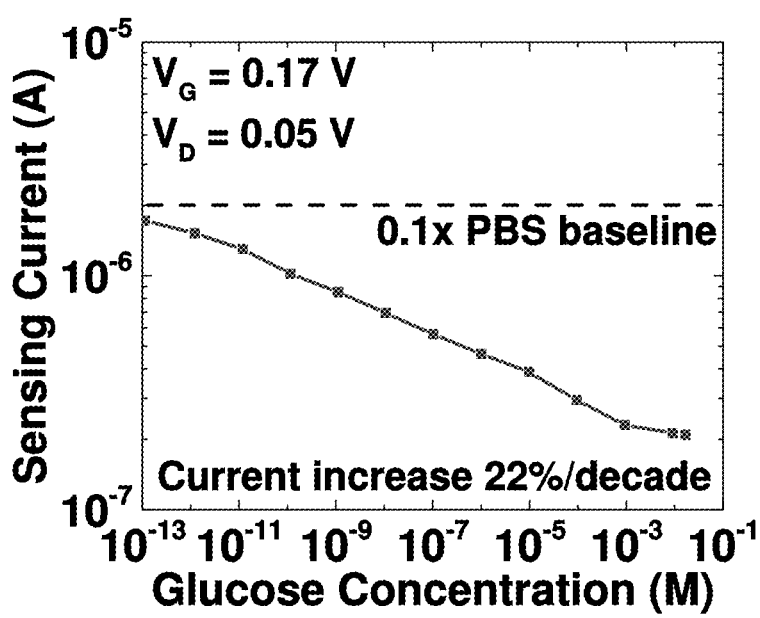
FIG. 15 is a plot of sensing current versus glucose concentration with gate voltage $V_G$ equal to 0.17 V and with drain voltage VD equal to 0.05 V in the device, according to an embodiment of the present disclosure.

FIG. 15 is a plot of sensing current versus glucose concentration with gate voltage $V_G$ equal to 0.17 V and with drain voltage VD equal to 0.05 V in the sensor device, according to an embodiment of the present disclosure. The sensing current increases by 22% when the glucose concentration decreases by one decade.

Figure 16:
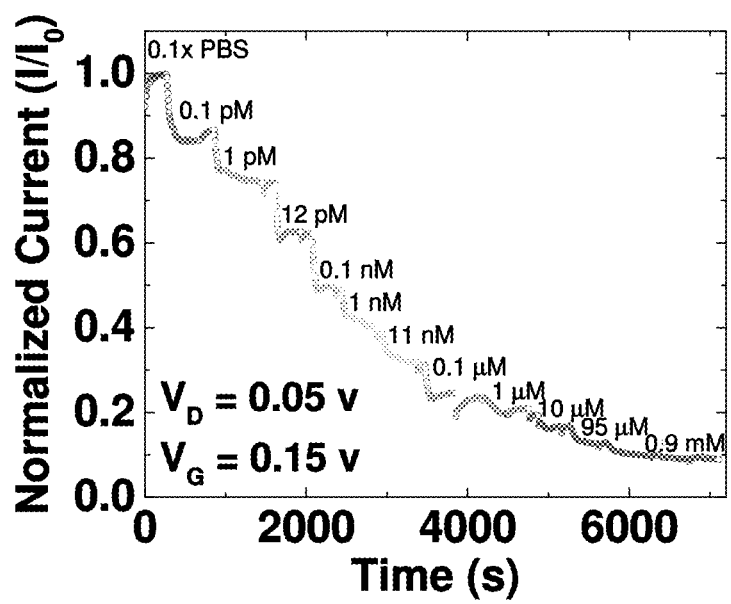
FIG. 16 is a plot of the normalized current versus time with gate voltage $V_G$ equal to 0.15 V and with drain voltage VD equal to 0.05 V, according to an embodiment of the present disclosure.

FIG. 16 is a plot of the normalized current versus time with gate voltage $V_G$ equal to 0.15 V and with drain voltage VD equal to 0.05 V, according to an embodiment of the present disclosure. As shown in FIG. 16, 3 pM glucose added into PBS baseline causes 18% of signal or current change. This clearly shows that the sensitivity of present glucose sensor is better than other conventional non-enzymatic glucose sensing results. Furthermore, the present glucose sensor provides a wider optimum sensing range between $10^{-11}$ M and $10^{-5}$ M. The optimum sensing concentration range can be tuned by adjusting a sensing area and modifying the receptor for a specific application.

Table 1 below provides examples of ranges of glucose concentration that is present in various bodily fluids. The present glucose sensor is able to detect glucose at the concentrations listed in Table 1. Therefore, the application of the present glucose sensor has broad application in the medical field and environment.

TABLE 1

Glucose Concentration Chart

| Environment | Concentration |
| --- | --- |
| Blood | 2-30 mM |
| Urine | 0.8-5.55 mM |
| Saliva | 8-210 μM |
| Sweat | 5-20 mM |
| Tear | 0.1-0.6 mM |

Although, the present sensor is described herein in this example for the specific application of glucose sensing, it is also contemplated the application of the sensor for sensing other molecules, for example, pesticides in produce, water pollution, etc. This can be accomplished by the selection of an appropriate receptor layer 64 in sensor 50.

As it can appreciated from the above paragraphs, an effective solution-processing procedure for fabricating ultra-thin, sensitive $In_2O_3$ semiconductor-based FETs for use as chemical biosensors is described herein. For example, one-step spin coating of aqueous $In_2O_3$ solution formed nanometer-thick (3.5 nm), smooth, and highly uniform films over large fabrication areas. The $In_2O_3$-based FETs achieve a mobility and on/off ratios of ~20 $cm^2 \cdot V^{-1} \cdot s^{-1}$ and over $10^7$, respectively. Liquid-gated FETs for biosensing platforms have low voltage driving and stable behavior. Specific chemical treatment such asapplying a receptor layer formed on a silane functionalization layer described in the above paragraphs and enzyme immobilization of $In_2O_3$-based FET biosensors provide pH and glucose detection, respectively, in real-time with linear and fast responses. This ultrathin biosensor platform is advantageous as a conformal sensor via delamination. The obtained devices have excellent contact on highly rough artificial skin surfaces and an artificial eye surface.

REFERENCES

1. Kim, D. H., et al. Dissolvable Films of Silk Fibroin for Ultrathin Conformal Bio-Integrated Electronics. *Nature Mater.* 2010, 9, 511-517.
2. Kim, S. Y.; Park, S.; Park, H. W.; Park, D. H.; Jeong, Y.; Kim, D. H. Highly Sensitive and Multimodal All-Carbon Skin Sensors Capable of Simultaneously Detecting Tactile and Biological Stimuli. *Adv. Mater.* 2015, 27, 4105.
3. Ryu, S.; Lee, P.; Chou, J. B.; Xu, R.; Zhao, R.; Hart, A. J.; Kim, S. G. Extremely Elastic Wearable Carbon Nanotube Fiber Strain Sensor for Monitoring of Human Motion. *ACS Nano* 2015, 9, 5929-5936.
4. Wang, C.; Hwang, D.; Yu, Z.; Takei, K.; Park, J.; Chen, T.; Ma, B.; Javey, A. User-Interactive Electronic Skin for Instantaneous Pressure Visualization. *Nature Mater.* 2013, 12, 899-904.
5. Sekitani, T.; Noguchi, Y.; Hata, K.; Fukushima, T.; Aida, T.; Someya, T. A Rubberlike Stretchable Active Matrix Using Elastic Conductors. *Science* 2008, 321, 1468-1472.
6. Takei, K.; Takahashi, T.; Ho, J. C.; Ko, H.; Gillies, A. G.; Leu, P. W.; Fearing, R. S.; Javey, A. Nanowire Active-Matrix Circuitry for Low-Voltage Macroscale Artificial Skin. *Nature Mater.* 2010, 9, 821-826.
7. Someya, T.; Sekitani, T.; Iba, S.; Kato, Y.; Kawaguchi, H.; Sakurai, T. A Large-Area, Flexible Pressure Sensor Matrix with Organic Field-Effect Transistors for Artificial Skin Applications. *Proc. Natl. Acad. Sci. U.S.A.* 2004, 101, 9966-9970.
8. Mannsfeld, S. C. B.; Tee, B. C. K.; Stoltenberg, R. M.; Chen, C. V. H. H.; Barman, S.; Muir, B. V. O.; Sokolov, A. N.; Reese, C.; Bao, Z. N. Highly Sensitive Flexible Pressure Sensors with Microstructured Rubber Dielectric Layers. *Nature Mater.* 2010, 9, 859-864.
9. Maheshwari, V.; Saraf, R. F. High-Resolution Thin-Film Device to Sense Texture by Touch. *Science* 2006, 312, 1501-1504.
10. Kim, D. H., et al. Epidermal Electronics. *Science* 2011, 333, 838-843.
11. Someya, T.; Kato, Y.; Sekitani, T.; Iba, S.; Noguchi, Y.; Murase, Y.; Kawaguchi, H.; Sakurai, T. Conformable, Flexible, Large-Area Networks of Pressure and Thermal Sensors with Organic Transistor Active Matrixes. *Proc. Natl. Acad. Sci. U.S.A.* 2005, 102, 12321-12325.
12. Takahashi, T.; Takei, K.; Gillies, A. G.; Fearing, R. S.; Javey, A. Carbon Nanotube Active-Matrix Backplanes for Conformal Electronics and Sensors. *Nano Lett.* 2011, 11, 5408-5413.
13. Hammock, M. L.; Chortos, A.; Tee, B. C.; Tok, J. B.; Bao, Z. 25th Anniversary Article: The Evolution of Electronic Skin (E-Skin): A Brief History, Design Considerations, and Recent Progress. *Adv Mater* 2013, 25, 5997-6038.
14. Claussen, J. C.; Kumar, A.; Jaroch, D. B.; Khawaja, M. H.; Hibbard, A. B.; Porterfield, D. M.; Fisher, T. S. Nanostructuring Platinum Nanoparticles on Multilayered Graphene Petal Nanosheets for Electrochemical Biosensing. *Adv. Funct. Mater.* 2012, 22, 3399-3405.

15. Dzyadevych, S. V.; Soldatkin, A. P.; El'skaya, A. V.; Martelet, C.; Jaffrezic-Renault, N. Enzyme Biosensors Based on Ion-Selective Field-Effect Transistors. *Anal. Chim. Acta.* 2006, 568, 248-258.

16. Zou, Y.; Xiang, C.; Sun, L. X.; Xu, F. Glucose Biosensor Based on Electrodeposition of Platinum Nanoparticles onto Carbon Nanotubes and Immobilizing Enzyme with Chitosan-$SiO_2$ Sol-Gel. *Biosens. Bioelectron.* 2008, 23, 1010-1016.

17. Cheng, Y.; Xiong, P.; Yun, C. S.; Strouse, G. F.; Zheng, J. P.; Yang, R. S.; Wang, Z. L. Mechanism and Optimization of Ph Sensing Using $SnO_2$ Nanobelt Field Effect Transistors. *Nano Lett.* 2008, 8, 4179-4184.

18. Windmiller, J. R.; Wang, J. Wearable Electrochemical Sensors and Biosensors: A Review. *Electroanal.* 2013, 25, 29-46.

19. Seung, W., et al. Nanopatterned Textile-Based Wearable Triboelectric Nanogenerator. *ACS Nano* 2015, 9, 3501-3509.

20. Roh, E.; Hwang, B. U.; Kim, D.; Kim, B. Y.; Lee, N. E. Stretchable, Transparent, Ultrasensitive, and Patchable Strain Sensor for Human-Machine Interfaces Comprising a Nanohybrid of Carbon Nanotubes and Conductive Elastomers. *ACS Nano* 2015, 9, 6252-6261.

21. Ha, M.; Park, J.; Lee, Y.; Ko, H. Triboelectric Generators and Sensors for Self-Powered Wearable Electronics. *ACS Nano* 2015, 9, 3421-3427.

22. Choi, S., et al. Stretchable Heater Using Ligand-Exchanged Silver Nanowire Nanocomposite for Wearable Articular Thermotherapy. *ACS Nano* 2015, 9, 6626-6633.

23. Li, C.; Lei, B.; Zhang, D.; Liu, X.; Han, S.; Tang, T.; Rouhanizadeh, M.; Hsiai, T.; Zhou, C. Chemical Gating of $In_2O_3$ Nanowires by Organic and Biomolecules. *Appl. Phys. Lett.* 2003, 83, 4014-4016.

24. Allen, B. L.; Kichamb are, P. D.; Star, A. Carbon Nanotube Field-Effect-Transistor-Based Biosensors. *Adv. Mater.* 2007, 19, 1439-1451.

25. Chen, K.-I.; Li, B.-R.; Chen, Y.-T. Silicon Nanowire Field-Effect Transistor-Based Biosensors for Biomedical Diagnosis and Cellular Recording Investigation. *Nano Today* 2011, 6, 131-154.

26. Kim, J., et al. Fabrication of High-Performance Ultrathin $In_2O_3$ Film Field-Effect Transistors and Biosensors Using Chemical Lift-Off Lithography. *ACS Nano* 2015, 9, 4572-4582.

27. Torsi, L.; Tafuri, A.; Cioffi, N.; Gallazzi, M. C.; Sassella, A.; Sabbatini, L.; Zambonin, P. G. Regioregular Polythiophene Field-Effect Transistors Employed as Chemical Sensors. *Sensor Actuat. B-Chem.* 2003, 93, 257-262.

28. Kuila, T.; Bose, S.; Khanra, P.; Mishra, A. K.; Kim, N. H.; Lee, J. H. Recent Advances in Graphene-Based Biosensors. *Biosens. Bioelectron.* 2011, 26, 4637-4648.

29. Sun, D. M.; Liu, C.; Ren, W. C.; Cheng, H. M. A Review of Carbon Nanotube- and Graphene-Based Flexible Thin-Film Transistors. *Small* 2013, 9, 1188-1205.

30. Sarkar, D.; Liu, W.; Xie, X. J.; Anselmo, A. C.; Mitragotri, S.; Banerjee, K. Correction to $MoS_2$ Field-Effect Transistor for Next-Generation Label-Free Biosensors. *ACS Nano* 2014, 8, 5367-5367.

31. Sarkar, D.; Liu, W.; Xie, X. J.; Anselmo, A. C.; Mitragotri, S.; Banerjee, K. Most Field-Effect Transistor for Next-Generation Label-Free Biosensors. *ACS Nano* 2014, 8, 3992-4003.

32. Rogers, J. A.; Someya, T.; Huang, Y. G. Materials and Mechanics for Stretchable Electronics. *Science* 2010, 327, 1603-1607.

33. Park, Y. J.; Lee, S. K.; Kim, M. S.; Kim, H.; Ahn, J. H. Graphene-Based Conformal Devices. *ACS Nano* 2014, 8, 7655-7662.

34. Porchetta, A.; Idili, A.; Vallee-Belisle, A.; Ricci, F. General Strategy to Introduce Ph-Induced Allostery in DNA-Based Receptors to Achieve Controlled Release of Ligands. *Nano Lett.* 2015, 15, 4467-4471.

35. Xiang, Y.; Lu, Y. Using Personal Glucose Meters and Functional DNA Sensors to Quantify a Variety of Analytical Targets. *Nature Chem.* 2011, 3, 697-703.

36. Tian, K.; Prestgard, M.; Tiwari, A. A Review of Recent Advances in Nonenzymatic Glucose Sensors. *Mater. Sci. Eng. C Mater. Biol. Appl.* 2014, 41, 100-118.

37. Badugu, R.; Lakowicz, J. R.; Geddes, C. D. Ophthalmic Glucose Sensing: A Novel Monosaccharide Sensing Disposable and Colorless Contact Lens. *Analyst* 2004, 129, 516-521.

38. Neithercott, T. The Future Is Near. 14 Diabetes Products Suggest Big Things to Come. *Diabetes Forecast* 2015, 68, 33-35.

39. Daum, K. M.; Hill, R. M. Human Tear Glucose. *Invest. Ophthalmol. Vis. Sci.* 1982, 22, 509-514.

40. Rim, Y. S.; Jeong, W. H.; Kim, D. L.; Lim, H. S.; Kim, K. M.; Kim, H. J. Simultaneous Modification of Pyrolysis and Densification for Low-Temperature Solution-Processed Flexible Oxide Thin-Film Transistors. *J. Mater. Chem.* 2012, 22, 25492-25492.

41. Rim, Y. S.; Chen, H. J.; Kou, X. L.; Duan, H. S.; Zhou, H. P.; Cai, M.; Kim, H. J.; Yang, Y. Boost up Mobility of Solution-Processed Metal Oxide Thin-Film Transistors via Confining Structure on Electron Pathways. *Adv. Mater.* 2014, 26, 4273-4278.

42. Rim, Y. S.; Chen, H. J.; Liu, Y. S.; Bae, S. H.; Kim, H. J.; Yang, Y. Direct Light Pattern Integration of Low-Temperature Solution-Processed All-Oxide Flexible Electronics. *ACS Nano* 2014, 8, 9680-9686.

43. Chen, H.; Rim, Y. S.; Jiang, C.; Yang, Y. Low-Impurity High Performance Solution-Processed Metal Oxide Semiconductors via a Facile Redox Reaction.Pdf>. *Chem. Mater.* 2015, 27, 4713-4718.

44. Huang, X.; Yeo, W. H.; Liu, Y. H.; Rogers, J. A. Epidermal Differential Impedance Sensor for Conformal Skin Hydration Monitoring. *Biointerphases* 2012, 7.

45. Chaudhury, M. K.; Whitesides, G. M. Direct Measurement of Interfacial Interactions between Semispherical Lenses and Flat Sheets of Poly(dimethylsiloxane) and Their Chemical Derivatives. *Langmuir* 1991, 7, 1013-1025.

46. Cui, Y.; Wei, Q.; Park, H.; Lieber, C. M. Nanowire Nanosensors for Highly Sensitive and Selective Detection of Biological and Chemical Species. *Science* 2001, 293, 1289-1292.

47. Wilson, R.; Turner, A. P. F. Glucose-Oxidase—An Ideal Enzyme. *Biosens. Bioelectron.* 1992, 7, 165-185.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A method of producing a metal oxide semiconductor film for sensor devices, comprising:

mixing at least one of a metal nitrate or a hydrate of a metal nitrate precursor in a solvent to obtain a precursor solution;

depositing a layer of said precursor solution onto a surface of a substrate;

annealing said layer of said precursor solution to provide said metal oxide semiconductor film, wherein said metal oxide semiconductor film has a substantially uniform thickness of at least 3 nm thick and less than 10 nm thick; and functionalizing said metal oxide semiconductor film by attaching molecules on a surface of the metal oxide semiconductor film, said molecules being open to make contact with a fluid so as to provide a sensing metal oxide semiconductor film for detecting at least one component of said fluid or at least one physical property or chemical property of said fluid, wherein functionalizing the metal oxide semiconductor film comprises:

functionalizing the metal oxide semiconductor film by attaching at least one type of enzyme on the surface of said metal oxide semiconductor film, or functionalizing the metal oxide semiconductor film with a salinized (3-Aminopropyl)triethoxysilane (APTES) so that the sensing metal oxide semiconductor film is used to measure pH of said fluid, or both.

2. The method of claim 1, wherein said metal oxide semiconductor film is a substantially amorphous film.

3. The method of claim 1, wherein said substantially uniform thickness is uniform to within a root-mean-square deviation of less than 10%.

4. The method of claim 1, wherein said substantially uniform thickness is uniform to within a root-mean-square deviation of less than 30%.

5. The method of claim 1, wherein said metal oxide semiconductor film has a substantially uniform thickness of at least 1 nm thick and less than 5 nm thick.

6. The method of claim 1, wherein said metal oxide semiconductor film has a substantially uniform thickness of about 3.5 nm thick.

7. The method of claim 1, wherein said solvent is water.

8. The method of claim 1, wherein said solvent is deionized water.

9. The method of claim 1, wherein said at least one of a metal nitrate or a hydrate of a metal nitrate precursor is indium nitrate hydrate.

10. The method of claim 1, wherein said at least one of a metal nitrate or a hydrate of a metal nitrate precursor is at least one of indium nitrate hydrate, zinc nitrate hydrate, aluminum nitrate hexahydrate, gallium nitrate hydrate, or titanium nitrate.

11. The method of claim 1, wherein said precursor solution has a concentration of said metal nitrate or a hydrate of a metal nitrate precursor within a range of 0.05 mole to 0.1 mole in solution.

12. The method of claim 1, wherein said annealing comprises a pre-baking to remove solvent from said layer after said depositing, and wherein said annealing further comprises a hard-baking of said layer to form an oxide film.

13. The method of claim 12, wherein said pre-baking is performed at about 100° C. and said hard-baking is performed at about 250° C.

14. The method of claim 1, wherein said substrate is a flexible substrate.

15. The method of claim 1, wherein said substrate is at least one of a glass substrate, a silicon substrate, polymer substrate, and metal substrate.

16. The method of claim 1, wherein said substrate has a thickness of at least 0.5 µm and less than 2 µm.

17. The method of claim 1, wherein said at least one type of enzyme is a glucose oxidase so that the sensing metal oxide semiconductor film is used to detect glucose in said fluid.

* * * * *